United States Patent
Naito et al.

(10) Patent No.: US 9,569,826 B2
(45) Date of Patent: Feb. 14, 2017

(54) RADIOGRAPHIC IMAGE PROCESSING DEVICE, RADIOGRAPHIC IMAGE PROCESSING METHOD, AND RECORDING MEDIUM

(71) Applicant: FUJIFILM Corporation, Tokyo (JP)

(72) Inventors: Satoshi Naito, Kanagawa (JP); Takahiro Kawamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/863,574

(22) Filed: Sep. 24, 2015

(65) Prior Publication Data

US 2016/0093030 A1    Mar. 31, 2016

(30) Foreign Application Priority Data

Sep. 30, 2014  (JP) ................................. 2014-199895

(51) Int. Cl.
| | |
|---|---|
| *G06K 9/00* | (2006.01) |
| *G06T 5/00* | (2006.01) |
| *A61B 6/00* | (2006.01) |
| *G06T 7/00* | (2006.01) |

(52) U.S. Cl.
CPC ............ *G06T 5/009* (2013.01); *A61B 6/5205* (2013.01); *A61B 6/5282* (2013.01); *G06T 7/0012* (2013.01); *G06T 2207/10116* (2013.01); *G06T 2207/20208* (2013.01)

(58) Field of Classification Search
None
See application file for complete search history.

(56) References Cited

U.S. PATENT DOCUMENTS

| | | | | |
|---|---|---|---|---|
| 7,046,757 | B1* | 5/2006 | Bani-Hashemi | A61B 6/032 348/E5.086 |
| 2005/0078799 | A1* | 4/2005 | Ancelin | A61B 6/502 378/154 |

FOREIGN PATENT DOCUMENTS

| | | |
|---|---|---|
| JP | 3423828 B2 | 7/2003 |
| JP | 3540914 B2 | 7/2004 |

OTHER PUBLICATIONS

Hideki Kato, "A New Method for Eliminating Scatter Components from a Digital X-ray Image by Later Processing", Journal of Japanese Society of Radiological Technology, Sep. 2006, pp. 1359-1368, vol. 62, No. 9.

* cited by examiner

*Primary Examiner* — Atiba O Fitzpatrick
(74) *Attorney, Agent, or Firm* — Sughrue Mion, PLLC

(57) ABSTRACT

A radiographic image processing device includes: an image acquisition section that acquires a subject image detected by a shielded detection portion and a non-shielded detection portion; an area information acquisition section that acquires area information which is information for specifying a non-shielded image area and a shielded image area; and a scattered ray suppression section that estimates spreading of scattered rays generated in a non-shielded subject portion, estimates that scattered rays that spread to the non-shielded image area from a shielded subject portion are not present, calculates a scattered ray component in each position in the non-shielded image area as the estimated scattered rays reach each position in the non-shielded image area, and suppresses the scattered ray component in each position in the non-shielded image area according to the calculated scattered ray component.

14 Claims, 4 Drawing Sheets

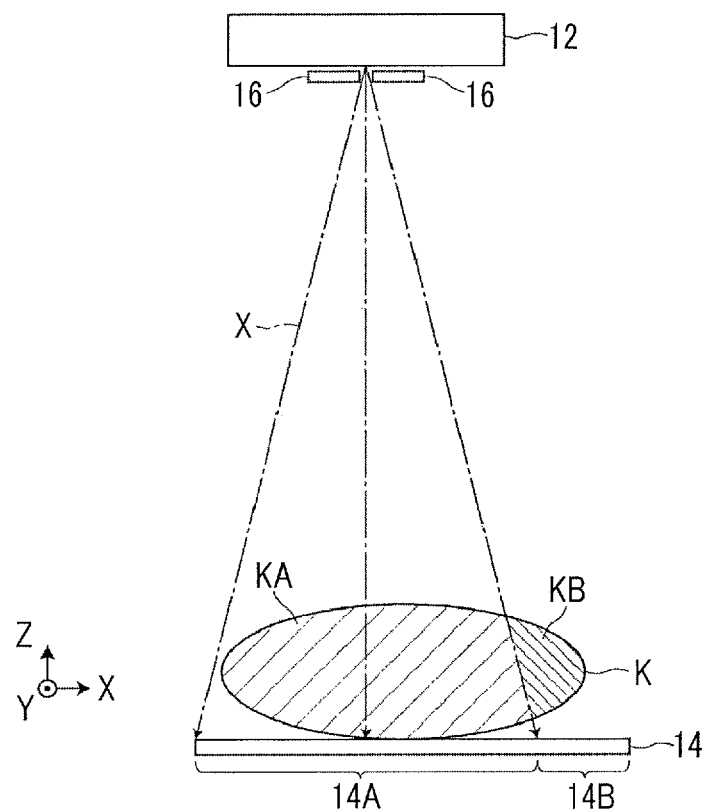
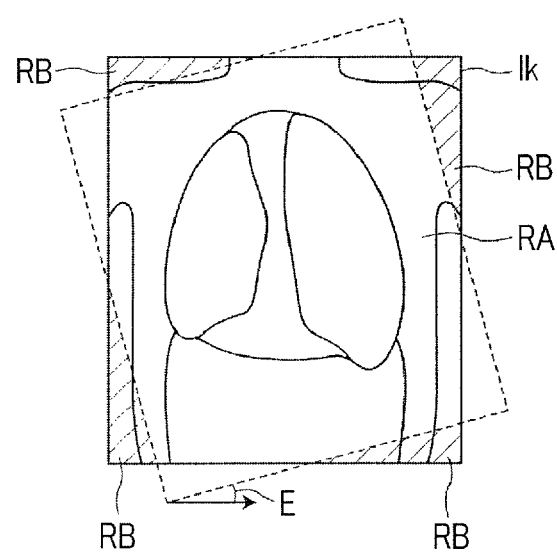

RADIOGRAPHIC IMAGE PROCESSING DEVICE, RADIOGRAPHIC IMAGE PROCESSING METHOD, AND RECORDING MEDIUM

CROSS-REFERENCE TO RELATED APPLICATIONS

The present application claims priority under 35 U.S.C. §119 to Japanese Patent Application No. 2014-199895, filed on Sep. 30, 2014. Each of the above application(s) is hereby expressly incorporated by reference, in its entirety, into the present application.

BACKGROUND OF THE INVENTION

1. Field of the Invention

The present invention relates to a radiographic image processing device and a radiographic image processing method that perform image processing with respect to a radiographic image, and a recording medium on which a program for causing a computer to execute the radiographic image processing method is recorded.

2. Description of the Related Art

In the related art, when capturing a radiographic image of a subject by using radioactive rays that pass through the subject, if the thickness of the subject is especially large, the radioactive rays are scattered inside the subject, and the contrast of the acquired radiographic image may deteriorate due to the scattered radioactive rays (hereinafter, referred to as scattered rays).

In order to solve such a problem, various techniques for suppressing a scattered ray component from a radiographic image of a subject using image processing have been proposed. For example, JP3423828B, JP3540914B, and Non-Patent Document "A New Method for Eliminating Scattered Ray Components from a Digital X-ray Image by Laser Processing", Hideki Kato, Journal of Japanese Society of Radiological Technology, Vol. 62, No. 9, 2006-09, pp. 1359-1368, provide a technique for calculating a scattered ray component of scattered rays that reach each position in a subject image based on a relational expression indicating an intensity distribution function of scattered rays corresponding to the thickness of a subject, and reducing the calculated scattered ray component from a pixel value of a corresponding position in the subject image, to thereby suppress the scattered ray component.

SUMMARY OF THE INVENTION

However, in an imaging system that includes a radiation source that emits radioactive rays to a subject, and a radiation detector that detects radioactive rays that pass through the subject, there is a case where an irradiation range from the radiation source is limited by a shield such as an irradiation field diaphragm, and thus, a subject image acquired by radiography of the subject becomes an image having a non-shielded image area indicating an image in the irradiation range of the radioactive rays from the radiation source and a shielded image area indicating an image outside of the irradiation range of the radioactive rays from the radiation source. When the technique disclosed in JP3423828B, JP3540914B, and the above-mentioned Non-Patent Document is applied with respect to the subject image, there is a possibility that an intensity distribution of the scattered rays corresponding to a shielded subject portion in which radioactive rays are shielded by the shield in an irradiation direction of the radioactive rays is erroneously estimated, and thus, the scattered rays that reach the non-shielded image area of the subject image may be excessive.

The present invention is made in view of the above-mentioned problems to provide a technique capable of reducing, with respect to a subject image having a shielded image area and a non-shielded image area, erroneous estimation of a scattered ray component in the non-shielded image area to thereby appropriately suppress the scattered ray component in the non-shielded image area of the subject image.

According to an aspect of the invention, there is provided a radiographic image processing device including: an image acquisition section that acquires a subject image which is a radiographic image captured by an imaging system that includes a radiation source that irradiates a subject with radioactive rays, a shield that partially shields the radioactive rays emitted to the subject, and a radiation detector that detects the radioactive rays passed through the subject, the subject image being detected under a predetermined imaging condition by a shielded detection portion which is a portion of the radiation detector where the radioactive rays are shielded by the shield in an irradiation direction of the radioactive rays from the radiation source and a non-shielded detection portion which is a portion of the radiation detector excluding the shielded detection portion; an area information acquisition section that acquires area information which is information for specifying a non-shielded image area indicating a pixel value corresponding to each position in the non-shielded detection portion in the subject image and a shielded image area indicating a pixel value corresponding to each position in the shielded detection portion in the subject image; and a scattered ray suppression section that estimates, based on the imaging condition and the area information, spreading of scattered rays generated in a non-shielded subject portion which is a portion of the subject that transmits the radioactive rays in the irradiation direction of the radioactive rays from the radiation source in the subject image, estimates that scattered rays that spread to the non-shielded image area from a shielded subject portion which is a portion of the subject where the radioactive rays are shielded by the shield in the irradiation direction of the radioactive rays from the radiation source are not present, calculates a scattered ray component in each position in the non-shielded image area as the estimated scattered rays reach each position in the non-shielded image area, and suppresses the scattered ray component in each position in the non-shielded image area according to the calculated scattered ray component.

According to another aspect of the invention, there is provided a radiographic image processing method, including: acquiring a subject image which is a radiographic image captured by an imaging system that includes a radiation source that irradiates a subject with radioactive rays, a shield that partially shields the radioactive rays emitted to the subject, and a radiation detector that detects the radioactive rays passed through the subject, the subject image being detected under a predetermined imaging condition by a shielded detection portion which is a portion of the radiation detector where the radioactive rays are shielded by the shield in an irradiation direction of the radioactive rays from the radiation source and a non-shielded detection portion which is a portion of the radiation detector excluding the shielded detection portion; acquiring area information which is information for specifying a non-shielded image area indicating a pixel value corresponding to each position in the non-shielded detection portion in the subject image and a shielded image area indicating a pixel value corresponding to each position in the shielded detection portion in the subject image; and estimating, based on the imaging condition and the area information, spreading of scattered rays generated in a non-shielded subject portion which is a portion of the subject that transmits the radioactive rays in the irradiation direction of the radioactive rays from the radiation source in the subject image, estimating that scattered rays that spread to the non-shielded image area from a shielded subject portion which is a portion of the subject where the radioactive rays are shielded by the shield in the irradiation direction of the radioactive rays from the radiation source are not present, calculating a scattered ray component in each position in the non-shielded image area as the estimated scattered rays reach each position in the non-shielded image area, and suppressing the scattered ray component in each position in the non-shielded image area according to the calculated scattered ray component.

According to still another aspect of the invention, there is provided a non-transitory computer-readable recording medium that stores a radiographic image processing program that causes a computer to function as: an image acquisition section that acquires a subject image which is a radiographic image captured by an imaging system that includes a radiation source that irradiates a subject with radioactive rays, a shield that partially shields the radioactive rays emitted to the subject, and a radiation detector that detects the radioactive rays passed through the subject, the subject image being detected under a predetermined imaging condition by a shielded detection portion which is a portion of the radiation detector where the radioactive rays are shielded by the shield in an irradiation direction of the radioactive rays from the radiation source and a non-shielded detection portion which is a portion of the radiation detector excluding the shielded detection portion; an area information acquisition section that acquires area information which is information for specifying a non-shielded image area indicating a pixel value corresponding to each position in the non-shielded detection portion in the subject image and a shielded image area indicating a pixel value corresponding to each position in the shielded detection portion in the subject image; and a scattered ray suppression section that estimates, based on the imaging condition and the area information, spreading of scattered rays generated in a non-shielded subject portion which is a portion of the subject that transmits the radioactive rays in the irradiation direction of the radioactive rays from the radiation source in the subject image, estimates that scattered rays that spread to the non-shielded image area from a shielded subject portion which is a portion of the subject where the radioactive rays are shielded by the shield in the irradiation direction of the radioactive rays from the radiation source are not present, calculates a scattered ray component in each position in the non-shielded image area as the estimated scattered rays reach each position in the non-shielded image area, and suppresses the scattered ray component in each position in the non-shielded image area according to the calculated scattered ray component.

The "shield that partially shields the radioactive rays emitted to the subject" means a shield that is positioned between a radiation source and a subject and shields at least a part of radioactive rays that are emitted from the radiation source and contribute to formation of a subject image. As long as the shield is capable of substantially shielding radioactive rays emitted to the subject from the radiation source, the shield may have an arbitrary shape, an arbitrary structure and an arbitrary material, and may be disposed in an arbitrary position between the radiation source and the subject. The shield may be an irradiation field diaphragm (collimator), for example.

The "shielded detection portion which is a portion of the radiation detector where the radioactive rays are shielded by the shield in the irradiation direction of the radioactive rays from the radiation source" means a detector portion where the shield is positioned between the radiation source and the detector in the irradiation direction of the radioactive rays emitted when a subject image is captured by radiography in the detector.

The "shielded subject portion which is a portion of the subject in which the radioactive rays are shielded by the shield in the irradiation direction of the radioactive rays from the radiation source" means a subject portion where the shield is positioned between the radiation source and the subject in the irradiation direction of the radioactive rays that are emitted when a subject image is captured by radiography in the subject and contribute to formation of the subject image.

The "non-shielded subject portion which is a portion or the subject that transmits the radioactive rays in the irradiation direction" means a subject portion that transmits the radioactive rays in the irradiation direction of the radioactive rays that are emitted when the subject image is captured by radiography in the subject and contribute to formation of the subject image.

The "estimating spreading of scattered rays generated in the non-shielded subject portion" means estimation of spreading of the scattered rays generated at least in the non-shielded subject portion It also may include estimation of spreading of scattered rays generated from other elements such as an air medium through which the radioactive rays that contribute to formation of the subject image pass when the subject image is captured by radiography, in addition to the spreading of the scattered ray generated in the non-shielded subject portion.

The "suppressing the scattered ray component in each position in the non-shielded image area according to the estimated scattered ray component" means reduction of the scattered ray component in such a manner that as the amount of the scattered ray component estimated in each position in the non-shielded image area becomes larger, the amount of the suppressed scattered ray component becomes larger.

Further, the "estimating that scattered rays that spread to the non-shielded image area from a shielded subject portion are not present" means reflection of a condition that the scattered rays that spread to the non-shielded image area from the shielded subject portion are not present as a condition setting of parameters or a necessary process is appropriately performed with respect to the scattered ray estimation function for estimating a scattered ray component in each position in the subject image, for example.

In the radiographic image processing device according to still another aspect of the invention, the scattered ray suppression section may estimate a spread distribution indicating spreading of scattered rays according to a primary ray component in each position in the subject image, and may calculate, with respect to each position in the non-shielded image area, the scattered ray component in each position in the non-shielded image area using a scattered ray estimation function for estimating a sum of scattered rays that reach each position in the non-shielded image area as a scattered ray component at the position, based on the estimated spread distribution of the scattered rays.

In this aspect, the scattered ray suppression section may set a first condition for negating the arrival of the scattered rays from the shielded subject portion in the scattered ray estimation function to estimate that the scattered rays that spread to the non-shielded image area from the shielded subject portion are not present. Alternatively, the scattered ray suppression section may set a second condition for setting the primary ray component in each position in the shielded image area to zero in the scattered ray estimation function to estimate that the scattered rays that spread to the non-shielded image area from the shielded subject portion are not present.

In the radiographic image processing device according to still another aspect of the invention, the scattered ray suppression section may subtract the scattered ray component in each position in the non-shielded image area from a pixel value in each corresponding position in the non-shielded image area to suppress the scattered ray component in each position in the non-shielded image area.

In the radiographic image processing device according to still another aspect of the invention, the scattered ray suppression section may separate a pixel value in each position in the non-shielded image area into a scattered ray component and a primary ray component, may reduce, in each position in the non-shielded image area, a scattered ray component corresponding to a first ratio from the scattered ray component at the position, and may reduce a primary ray component corresponding to a second ratio which is equal to or smaller than the first ratio from the primary ray component at the position, to suppress the scattered ray component in each position in the non-shielded image area.

The "first ratio" means the ratio of the amount of a scattered ray component removed from the amount of the entire scattered ray component to the amount of the entire scattered ray component, in each position in the non-shielded image area. Assuming that the amount of the entire scattered ray component in one position in the non-shielded image area is 1, the first ratio is set to a value that is greater than 0 and is equal to or smaller than 1. Further, the "second ratio" means the ratio of the amount of a primary ray component removed from the amount of the entire primary ray component with respect to the amount of the entire primary ray component, in each position in the non-shielded image area. The first and second ratios are appropriately set according to a necessary relative proportion of the scattered ray component with respect to the primary ray component.

According to the invention, it is possible to reduce erroneous estimation of a scattered ray component in a non-shielded image area, to thereby appropriately suppress the scattered ray component in the non-shielded image area of a subject image.

BRIEF DESCRIPTION OF THE DRAWINGS

FIG. 2 is a diagram illustrating a positional relationship between an imaging device and a subject when a subject image is captured by radiography.

FIG. 3 is a diagram illustrating a shielded image area and a non-shielded image area in a subject image.

DESCRIPTION OF THE PREFERRED EMBODIMENTS

Figure 1:
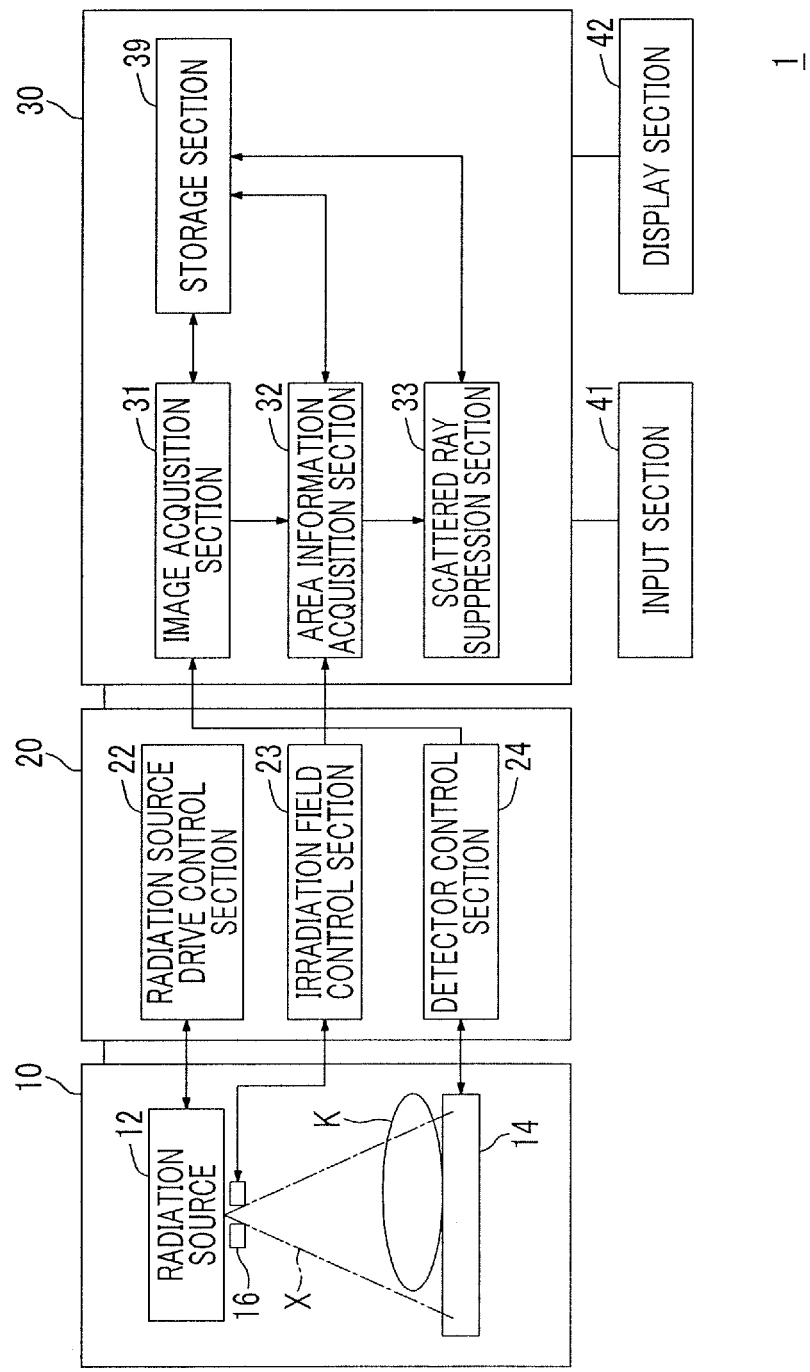
FIG. 1 is a block diagram schematically illustrating a configuration of a radiation imaging system to which a radiographic image processing device according to a first embodiment of the invention is applied.

Hereinafter, embodiments of the invention will be described with reference to the accompanying drawings. FIG. 1 is a block diagram schematically illustrating a configuration of a radiation imaging system 1 to which a radiographic image processing device according to a first embodiment of the invention is applied. As shown in FIG. 1, the radiation imaging system 1 according to this embodiment includes an imaging device 10, a control device 20 that controls the radiation imaging system 1, and a radiographic image processing device 30 (hereinafter, referred to as an image processing device 30).

The imaging device 10 includes a radiation source 12 that irradiates a subject K with radioactive rays X, a radiation detector 14 that detects X-rays that pass through the subject K to acquire a radiographic image of the subject K (hereinafter, referred to as a detector 14), and an irradiation field diaphragm 16.

In this embodiment, a scattered ray removal grid for removing scattered rays scattered by the subject K from the radioactive rays X that pass through the subject K is not disposed between the subject K and the detector 14.

The control device 20 includes a radiation source drive control section 22 that drive-controls the radiation source 12 according to a set imaging condition, a detector control section 24 that controls the detector 14 so that the detector 14 acquires a radiographic image, and an irradiation field control section 23 that controls lengths of a short side and a long side of an approximately rectangular opening of the irradiation field diaphragm 16 and a relative angle of the irradiation field diaphragm 16 with respect to the detector 14. The irradiation field control section 23 transmits opening area information of an irradiation field diaphragm 16 (the lengths of the short side and the long side of the approximately rectangular opening and the relative angle with respect to the detector 14) to an area information acquisition section 32 (which will be described later) as necessary.

The image processing device 30 is a computer that includes an input section 41 through which various inputs of an operator with respect to the image processing device 30 are input, a display section 42, a central processing unit (CPU), a semiconductor memory, a communication interface, and a storage section 39 such as a hard disk or an SSD. The image processing device 30 has a radiographic image processing program installed therein according to each embodiment. Further, by execution of such a radiographic image processing program, the CPU and the memory of the image processing device 30 cooperatively function as an image acquisition section 31 that acquires a subject image Ik captured by radiography of a subject K, an area information acquisition section 32, and a scattered ray suppression section 33. The input section 41 includes a keyboard, a mouse, a touch panel, or the like. Further, the display section 42 includes a CRT, a liquid crystal display, or the like, and performs display of a radiographic image acquired by the imaging device 10 or display of information necessary for various other desired processes.

The image acquisition section 31 acquires the subject image Ik captured by photography of the subject K.

The subject image Ik is captured under a predetermined imaging condition in a state where the irradiation field diaphragm (shield) 16 is positioned in the imaging device 10 so that radioactive rays from the radiation source 12 emitted to the subject K are partially shielded in an irradiation direction of the radioactive rays.

FIG. 2 is a diagram illustrating a positional relationship between the radiation source 12, the subject K, the detector 14, and the irradiation field diaphragm 16 in radiography of the subject image Ik, and FIG. 3 is a diagram illustrating a relationship between the subject image Ik, a non-shielded image area RA, and a shielded image area RB. Here, assuming that a short side direction of the detector 14 having an approximately rectangular shape is an X-direction, and a long side direction thereof is a Y-direction, the irradiation field diaphragm 16 is positioned to form an approximately rectangular opening in which a short side thereof has an inclination angle E with respect to the X-direction in an XY plane, and the radioactive rays X are emitted to an irradiation area corresponding to the positioned opening. Further, the subject K is positioned so that a body axis of the subject K is parallel to the Y-axis direction. If radiography is performed in the above-described positioning states, as shown in FIG. 2, a subject image Ik indicating the subject K is detected by a shielded detector portion 14B which is a detector portion in which the radioactive rays are shielded by the shield 16 in the irradiation direction of the radioactive rays from the radiation source 12 and a non-shielded detector portion 14A which is a detector portion in which the shielded detector portion 14B is excluded in the detector 14. In other words, the shielded detector portion 14B is a detector portion positioned outside of an irradiation range in the radiation source 12, and the non-shielded detector portion 14A is a detector portion positioned in the irradiation range in the radiation source 12.

As shown in FIG. 3, when radiography is performed in the positioning state as shown in FIG. 2, the subject image Ik detected by the detector 14 includes the shielded image area RB including a pixel value corresponding to each position in the shielded detector portion 14B, and the non-shielded image area RA including a pixel value corresponding to each position in the non-shielded detector portion 14A. A broken line in FIG. 3 indicates an area corresponding to an irradiation area. Further, as shown in FIG. 2, since an irradiation range of the radioactive rays X is limited by the irradiation field diaphragm 16, the radioactive rays X are directly incident on the a non-shielded subject portion KA which is a subject portion positioned in the irradiation range of the radioactive rays X in the subject K in the irradiation direction of the radioactive rays, and pass through the non-shielded subject portion KA. On the other hand, since the radioactive rays X are shielded in a shield subject portion KB which is a subject portion positioned outside of the irradiation range of the radioactive rays X by the irradiation field diaphragm 16 in the radioactive ray irradiation direction of the radioactive rays, the radioactive rays are not directly incident in the irradiation direction.

Here, the "shield that partially shields the radioactive rays emitted to the subject" means a shield that is positioned between a radiation source and a subject and shields at least a part of radioactive rays that are emitted from the radiation source and contribute to formation of a subject image. As long as the shield is capable of substantially shielding radioactive rays emitted to the subject from the radiation source, the shield may have an arbitrary structure and an arbitrary material, and may be disposed in an arbitrary position between the radiation source and the subject.

The area information acquisition section 32 acquires area information which is information for specifying the non-shielded image area RA including the pixel value corresponding to each position in the non-shielded detector portion 14A in the subject image Ik, and the shielded image area RB including the pixel value corresponding to each position in the shielded detector portion 14B in the subject image Ik. Here, the size of the detector 14 or the relative position of the detector 14 with respect to the irradiation field diaphragm 16 is known. The area information acquisition section 32 acquires area information by specifying the non-shielded image area RA and the shielded image area RB based on the opening area information in radiography of the subject image and the size of the detector 14 or the relative position of the detector 14 with respect to the irradiation field diaphragm 16 from the irradiation field control section 23.

Further, the area information acquisition section 32 may employ an arbitrary method for specifying the non-shielded image area RA and the shielded image area RB. For example, the area information acquisition section 32 may employ a method of recognizing an irradiation area in a radiographic image by a known image analysis technique (see JP1988-259538A (JP-S63-259538A), JP1998-275213 (JP-H10-275213A), or the like), and setting the recognized irradiation area as the non-shielded image area RA and setting a non-shielded image area of the radiographic image as the shielded image area RB. Further, the area information acquisition section 32 may employ a method of specifying an irradiation area in a radiographic image based on an opening shape of an irradiation field diaphragm and a relative positional relationship between a radiation source and a detector (see JP2010-200945A or the like), and setting the specified irradiation area as the non-shielded image area RA and setting a non-irradiation area of the radiographic image as the shielded image area RB.

The scattered ray suppression section 33 estimates, based on the imaging condition and the area information, spreading of scattered rays generated in the non-shielded subject portion KA, estimates that the scattered rays that spread to the non-shielded image area RA from the shielded subject portion KB are not present, calculates a scattered ray component in each position in the non-shielded image area RA as the estimated scattered rays reach each position in the non-shielded image area RA, and suppresses the scattered ray component in each position in the non-shielded image area RA according to the calculated scattered ray component.

Here, as disclosed in JP3423828B, JP3540914B, and the Non-Patent Document, a technique that individually calculates an intensity distribution of scattered rays indicating spreading of scattered rays due to a primary ray component that reaches each position in a subject image and suppresses, with respect to one target position in the subject image, the scattered ray component using a scattered ray estimation function for estimating a sum of scattered rays that spread according to the intensity distribution of the scattered rays from each position other than the target position in the subject image and reach the target position as the amount of a scattered ray component at the position is known. However, when this technique is applied to the subject image Ik having the shielded image area RB and the non-shielded image area RA as it is, the intensity distribution of scattered rays that spread from the shielded subject portion KB to the non-shielded image area RA is applied to estimate the scattered ray component, and at the target position in the non-shielded image area RA, the scattered rays that spread from the shielded subject portion KB where scattered rays are not generated to the non-shielded image area RA are mistakenly added, and thus, the amount of the scattered ray component may be excessive. Particularly, in a portion of the non-shielded image area RA which is close to the shielded image area RB, it is considered that such an error due to the scattered ray component is greater. The primary ray component means a radioactive ray component incident to a detector in the irradiation direction of the radioactive rays from the radiation source.

In view of the above problems, according to the embodiment of the invention, there is provided a technique capable of estimating spreading of scattered rays generated in a non-shielded subject portion KA, estimating that scattered rays that spread from a shielded subject portion KB to a non-shielded image area RA are not present, calculating a scattered ray component in each position in the non-shielded image area RA as the estimated scattered rays reach each position in the non-shielded image area RA, and suppresses the scattered ray component in each position in the non-shielded image area RA according to the calculated scattered ray component, to thereby reduce erroneous estimation of the scattered ray component in the non-shielded image area RA.

Specifically, the scattered ray suppression section 33 estimates a spread distribution indicating spreading of scattered rays according to a primary ray component in each position in the subject image Ik, and calculates, with respect to each position in the non-shielded image area RA, a scattered ray component in each position in the non-shielded image area RA based on the estimated spread distribution of the scattered rays using the scattered ray estimation function for estimating a sum of scattered rays that reach each position in the non-shielded image area RA as a scattered ray component at the position.

Here, the scattered ray suppression section 33 estimates a scattered ray image Is indicating a scattered ray component Is(x, y) in each position in the subject image Ik using the scattered ray estimation function defined in the following Expression (1). Here, Ip in Expression (1) is defined by Expression (2).

$$I_s(x, y) = \sum_{x', y'} I_p(x', y') \times KS(x, y, T_k(x', y'), \theta(x', y')) \times \delta(x', y') \quad (1)$$

$$I_p(x, y) = I_o(x, y) \times \exp(-T_k(x, y) \times \mu) \quad (2)$$

Here, (x, y) represents coordinates of the position in the subject image Ik, Ip(x, y) represents a pixel value corresponding to a primary ray component at a position (x, y), Is(x, y) represents a pixel value corresponding to a scattered ray component at the position (x, y), Io(x, y) represents a pixel value indicating the amount of arriving rays detected by the detector 14 at the position (x, y) when it is assumed that the subject K is not present (a pixel value indicating the amount of incident rays at a position on a subject surface corresponding to the position (x, y)), µ represents a linear attenuation coefficient of a subject, and KS(x, y, Tn(x', y'), θ(x', y')) represents a convolution kernel indicating a point spread function around a pixel position (x', y') (indicating a spread distribution of scattered rays). Further, such a convolution kernel KS is selected according to a thickness distribution Tk(x', y') of the subject K at the position (x', y') and a parameter θ(x', y') at the position (x', y'). Here, Io(x, y) is changed according to a distance (SID) between the radiation source 12 and a detection surface of the detector 14, a tube voltage, and the amount of imaging rays. Expression (2) is an expression based on a known index attenuation rule, and is an expression obtained by defining the pixel value Ip(x, y) corresponding to a primary ray component at the position (x, y) by the pixel value Io corresponding to such a position, a thickness distribution Tk(x, y) of the subject K, and the linear attenuation coefficient µ indicating a radiation absorption level of the subject K, with respect to each position in the subject image Ik.

The parameter θ(x', y') is a parameter for specifying the convolution kernel KS(x, y, Tk(x', y'), θ(x', y')) at the position (x', y'). Here, the parameter θ(x', y') is a parameter indicating an imaging condition, set for each imaging condition indicating the amount of imaging rays (the product of a tube current and irradiation time) and the tube voltage. The storage section 39 stores a table in which the thickness distribution Tk(x', y') of the subject, the parameter θ(x', y'), and the convolution kernel KS(x, y, Tk(x', y'), θ(x', y')) which are created in advance are associated with each other. Further, the scattered ray suppression section 33 uses the convolution kernel KS(x, y, Tk(x', y'), θ(x', y')) corresponding to the thickness distribution Tk(x', y') of the subject K in the subject image Ik and the parameter θ(x', y') corresponding to the imaging condition in radiography, with reference to the table for each position (x', y'), in Expression (1).

Further, in the scattered ray estimation function shown in Expression (1), the scattered ray component Is(x, y) is approximated by convolution of the point spread function (KS in Expression (1)) with respect to the primary ray component Ip. Further, the scattered ray estimation function shown in Expression (1) includes a delta function δ(x', y') for negating a spread distribution of scattered rays at each position in the shield image area RB and maintaining a spread distribution of scattered rays at each position in the non-shielded image area RA. Specifically, at each position (x', y') in the non-shielded image area RA, using δ(x', y')=1, a result of multiplying a pixel value Ip(x', y') of a primary ray component at each position and the convolution kernel KS(x, y, Tk(x', y'), θ(x', y')) is maintained. Further, at each position (x', y') in the shielded image area RB, using δ(x', y')=0, a result of multiplying a pixel value Ip(x', y') of a primary ray component at the position in the shielded image area RB and the convolution kernel KS(x, y, Tk(x', y'), θ(x', y')) is set to zero (negated). In this way, a first condition for negating scattered rays that spread from the shielded subject portion KB to the non-shielded image area RA is set in the scattered ray estimation function by the delta function δ, for reflection.

Further, in the scattered ray estimation function shown in Expression (1), a sum of scattered rays that reach the position (x, y) from each position (x', y') of the subject image Ik is defined as the pixel value Is(x, y) (the amount of a scattered ray component) corresponding to the scattered ray component of the position (x, y) based on the result of multiplying the pixel value Ip(x', y') of the primary ray component at the position, the convolution kernel KS(x, y, Tk(x', y'), θ(x', y')), and the delta function δ(x', y').

The spread distribution of scattered rays at each position changes according to the thickness of the subject, and also changes according to various variable elements such as an imaging condition, information indicating a composition of the subject, an air gap, or characteristics of a radiation detector. Thus, in the scattered ray estimation function as shown in Expression (1), the parameter θ(x', y') for specifying a point spread function may be set for each arbitrary combination of one or more elements selected from the various variable elements, and thus, the parameter θ(x', y') may be a parameter indicating each combination. Further, the imaging condition reflected in the parameter θ(x', y') may include, for example, an arbitrary combination of one or more elements selected from an imaging distance (SID) in imaging, the amount of imaging rays, a tube voltage, materials of a target of a radiation source and a filter, and the type of a radiation detector to be used in imaging. Here, the convolution kernel KS may be experimentally obtained according to the information indicating the thickness of the subject and the composition of the subject, the imaging condition, and the like.

The scattered ray suppression section 33 subtracts the scattered ray component in each position in the non-shielded image area RA from the pixel value in each corresponding position in the non-shielded image area RA in the subject image Ik to suppress the scattered ray component in each position in the non-shielded image area RA, to thereby acquire a scattered ray suppression image in which the scattered ray component is suppressed. Further, the scattered ray suppression section 33 stores the scattered ray suppression image in the storage section 39.

Here, the scattered ray suppression section 33 calculates the primary ray component in each position in the subject image Ik by Expression (1) to acquire an image indicating the primary ray component in each position in the subject image Ik as a primary ray image Ip, and calculates the scattered ray component in each position in the non-shielded image area RA by Expression (2) to acquire a scattered ray image Is indicating the pixel value Is(x, y) of scattered rays in each position in the non-shielded image area RA. Further, the scattered ray suppression section 33 aligns corresponding positions of the subject image Ik and the scattered ray image Is, subtracts the scattered ray image Is from the non-shielded image area RA to obtain a scattered ray suppressed image in which the scattered ray component is suppressed, and then, stores the scattered ray suppressed image in the storage section 39.

Further, the scattered ray suppression section 33 may employ an arbitrary function capable of indicating a spread distribution of scattered rays in each position in the subject image Ik as the scattered ray estimation function, and may set a condition that scattered rays that spread to the non-shielded image area RA from the shielded subject portion KB with respect to the shielded image area RB are not present by an arbitrary method.

For example, the scattered ray suppression section 33 may use Expression (3) instead of Expression (2). A scattered ray estimation function shown in Expression (3) includes a primary ray estimation function for estimating the pixel value Ip(x', y') of the primary ray component in each position in the non-shielded image area RA based on the index attenuation rule, and setting the pixel value Ip(x', y') of the primary ray component in each position in the shielded image area RB to zero. In Expression (3), a convolution kernel KS(x, y, Tk(x', y'), θ(x', y')) is the same as the convolution kernel KS(x, y, Tk(x', y'), θ(x', y')) Expression (2). The scattered ray estimation function in Expression (3) sets a second condition for setting the pixel value Ip(x', y') of the primary ray component in each position in the non-shielded image area RA to a value determined by Expression (1) and setting the pixel value Ip(x', y') of the primary ray component in each position in the shielded image area RB to zero so that the primary ray component in each position in the shielded image area RB is zero, in the scattered ray estimation function. Further, in the function shown in Expression (3), based on a result of multiplying the pixel value Ip(x', y') of the primary ray component in each position and the convolution kernel KS(x, y, Tk(x', y'), θ(x', y')), a sum of scattered rays that reach the position (x, y) from each position (x', y') of the subject image Ik is defined as the pixel value Is(x, y) (the amount of a scattered ray component) of the scattered ray component in the position (x, y).

$$I_s(x, y) = \sum_{x',y'} I_p(x', y') \times KS(x, y, T_k(x', y'), \theta(x', y')) \quad (3)$$

Figure 4:
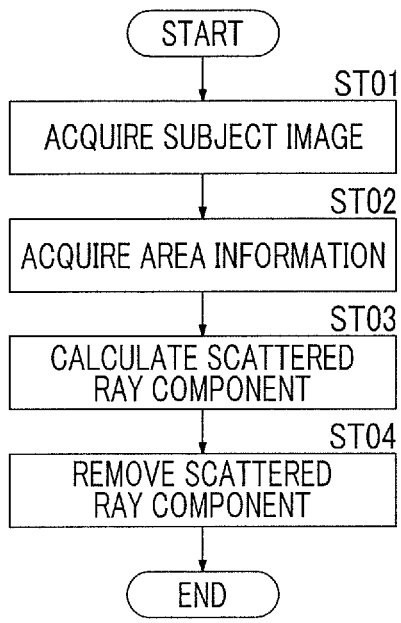
FIG. 4 is a flowchart illustrating a process performed in the radiographic image processing device in the first embodiment.

FIG. 4 is a flowchart illustrating a process performed by the image processing device 30 according to the first embodiment of the invention. The flow of the process performed by the image processing device 30 will be described with reference to FIG. 4.

First, the image acquisition section 31 acquires a subject image Ik (ST01). Then, the area information acquisition section 32 acquires area information on the subject image Ik (ST02). Subsequently, the scattered ray suppression section 33 calculates a scattered ray component Is(x, y) in each position in a non-shielded image area RA based on an imaging condition, the area information, and the conditional Expressions (1) and (2), and generates a scattered ray image Is indicating a scattered ray component in each position in the non-shielded image area RA (ST03). The scattered ray suppression section 33 subtracts the scattered ray image Is from the non-shielded image area RA (an image detected by the non-shielded detector portion 14A in the subject image Ik) to suppress the scattered ray component in each position in the non-shielded image area RA, to thereby acquire a scattered ray suppressed image in which the scattered ray component is suppressed (ST04). Further, the scattered ray suppression section 33 stores the scattered ray suppressed image in the storage section 39, and then, terminates the process. Then, the image processing device 30 performs predetermined image processing such as noise removal, grayscale processing and frequency processing on the scattered ray suppressed image as necessary to obtain a processed image, and stores the processed image in the storage section 39. Further, when a display request is received from a user, the image processing device 30 displays the processed image in the display section 42.

According to this embodiment, it is possible to estimate spreading of scattered rays generated in the non-shielded subject portion KA, to estimate that scattered rays that spread to the non-shielded image area RA from the shielded subject portion KB are not present, to calculate a scattered ray component in each position in the non-shielded image area RA as the estimated scattered rays reach each position in the non-shielded image area RA, and to suppress the scattered ray component in each position in the non-shielded image area RA according to the calculated scattered ray component, to thereby reduce erroneous estimation of the scattered ray component in the non-shielded image area RA, and thus, it is possible to appropriately suppress the scattered ray component in the non-shielded image area RA.

Further, as the scattered ray suppression section 33 estimates the spread distribution indicating the spreading of the scattered rays according to the primary ray component in each position in the subject image Ik, and calculates, with respect to each position in the non-shielded image area RA, the scattered ray component in each position in the non-shielded image area RA based on the estimated spread distribution of scattered rays using the scattered ray estimation function for estimating the sum of the scattered rays that reach the position in the non-shielded image area RA as the scattered ray component at the position, it is possible to appropriately estimate the scattered ray component in each position in the non-shielded image area RA.

Further, as shown in Expression (2), when the first condition for negating the arrival of the scattered rays from the shielded subject portion KB to the non-shielded image area RA is set in the scattered ray estimation function and the condition that the scattered rays that spread to the non-shielded image area RA from the shielded subject portion KB are not present are considered, it is possible to appropriately reduce erroneous estimation of the scattered ray component in each position in the non-shielded image area RA, to thereby appropriately suppress the scattered ray component from the non-shielded image area RA. Further, as shown in Expression (2), since the scattered ray estimation function includes the function for negating the spread distribution of the scattered rays in each position in the shielded image area RB and maintaining the spread distribution of the scattered rays in each position in the non-shielded image area RA, it is possible to set the first condition in the scattered ray estimation function by a relatively simple method.

Further, as shown in Expression (3), when the second condition for setting the primary ray component in each position in the shielded image area RB to zero is set in the scattered ray estimation function and the condition that the scattered rays that spread to the non-shielded image area RA from the shielded subject portion KB are not present are considered, it is possible to appropriately reduce erroneous estimation of the scattered ray component in each position in the non-shielded image area RA, to thereby appropriately suppress the scattered ray component from the non-shielded image area RA. Further, as shown in Expression (3), since the scattered ray estimation function includes the primary ray estimation function for estimating the pixel value $Ip(x', y')$ of the primary ray component in each position in the non-shielded image area RA based on the index attenuation rule and setting the pixel value $Ip(x', y')$ of the primary ray component in each position in the shielded image area RB to zero, it is possible to set the second condition in the scattered ray estimation function by a relatively simple method.

Further, since the scattered ray suppression section 33 subtracts the scattered ray component in each position in the non-shielded image area RA from the pixel value in each corresponding position in the non-shielded image area RA to suppress the scattered ray component in each position in the non-shielded image area RA, it is possible to provide a scattered ray processed image in which the scattered ray component of the subject image Ik is appropriately suppressed by a relatively simple method. Thus, when necessary image processing is further performed with respect to the scattered ray processed image to display the scattered ray processed image in the display section 42, it is possible to provide an image with high quality suitable for observation.

Further, the scattered ray suppression section 33 may employ an arbitrary method capable of reducing the scattered ray component in each position in the non-shielded image area RA estimated in the scattered ray estimation function. For example, as illustrated in a second embodiment of the invention, the scattered ray suppression section 33 may be configured to separate a pixel value in each position in the non-shielded image area RA into a scattered ray component and a primary ray component, to reduce, in each position in the non-shielded image area RA, a scattered ray component corresponding to a first ratio from the scattered ray component at the position, and to reduce a primary ray component corresponding to a second ratio which is equal to or smaller than the first ratio from the primary ray component at the position as necessary, to thereby suppress the scattered ray component in each position in the non-shielded image area RA.

Figure 5:
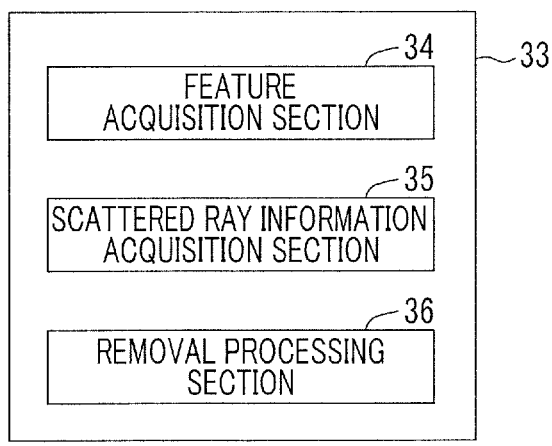
FIG. 5 is a schematic block diagram illustrating a configuration of a scattered ray control section according to a second embodiment.
Figure 6:
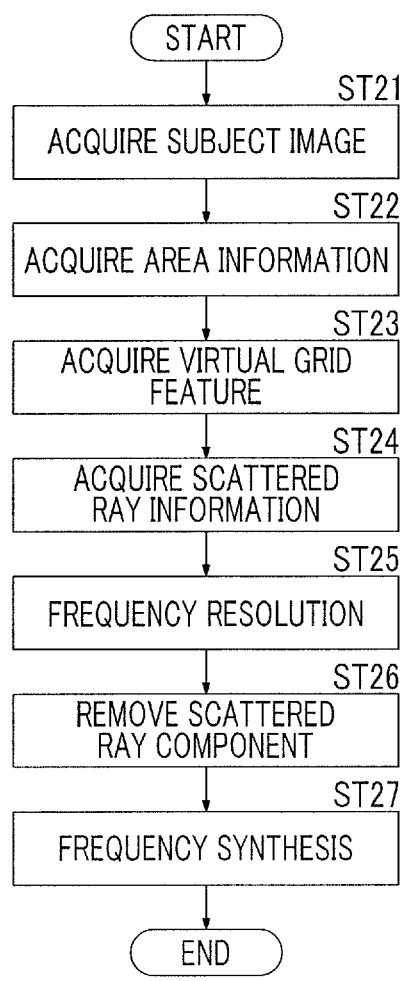
FIG. 6 is a flowchart illustrating a process performed in a radiographic image processing device in the second embodiment.

The second embodiment of the invention will be described with reference to FIGS. 5 and 6. FIG. 5 is a block diagram schematically illustrating a configuration of the scattered ray suppression section 33 according to the second embodiment of the invention. FIG. 6 is a flowchart illustrating a process performed by a radiographic image processing device according to the second embodiment of the invention.

As shown in FIG. 5, the image processing device 30 according to the second embodiment includes the scattered ray suppression section 33 that provides the same scattered ray removal effect as in a case where imaging is actually performed using a grid to a subject image acquired by performing imaging without using the grid. The second embodiment is different from the above-described each embodiment in that the scattered ray suppression section 33 includes a feature acquisition section 34 that acquires virtual grid features which are features of a virtual grid, a scattered ray information acquisition section 35 that acquires scattered ray information indicating a scattered ray component of scattered rays included in a subject image Ik as scattered ray information, and a removal processing section 36 that performs a scattered ray removal process of a non-shielded image area RA based on the virtual grid features acquired by the feature acquisition section 34 and the scattered ray information acquired by the scattered ray information acquisition section 35. In the second embodiment, since a process in the scattered ray suppression section 33 is different from the process in the scattered ray suppression section 33 in the first embodiment, but other configurations or functions are the same as those of the first embodiment, points which are different from those in the first embodiment will be mainly described. Further, the same reference numerals are given to the common parts, and description thereof will not be repeated.

The feature acquisition section 34 acquires a virtual gird feature by an input operation of an operator through the input section 41. In the second embodiment, the virtual grid features include a scattered ray transmissivity Ts for a virtual grid, and a transmissivity (primary ray transmissivity) Tp of primary rays that pass through a subject K and are directly incident to the detector 14. The scattered ray transmissivity Ts and the primary ray transmissivity Tp have a value of 0 to 1.

The feature acquisition section 34 may directly receive inputs of the values of the scattered ray transmissivity Ts and the primary ray transmissivity Tp to obtain the virtual grid features, but in the second embodiment, the feature acquisition section 34 receives at least one designation among grid information indicating the type of the grid, information on a subject (subject information), and an imaging condition when capturing the subject image Ik to obtain the virtual grid features, that is, the scattered ray transmissivity Ts and the primary ray transmissivity Tp. Hereinafter, the imaging condition used in the feature acquisition section 34 is referred to as a feature acquisition imaging condition.

Here, the grid information includes at least one piece of information among a variety of information for specifying the type of the grid, such as a grid ratio, a grid density, whether the grid is a convergence type or a parallel type, a focusing distance in the case of the convergence type, and an inter-space material (aluminum, fiber, Bakelite or the like).

The scattered ray transmissivity Ts and the primary ray transmissivity Tp change according to the type of grid. Thus, a table in which at least one of a variety of grid information and virtual grid features are associated with each other is stored in the storage section 39, with respect to the grid information.

The subject information represents the type of a subject such as a chest portion, an abdominal portion, or a head portion. Here, when capturing the subject image Ik, the type of a grid to be used is generally determined according to an imaging portion, and the scattered ray transmissivity Ts and the primary ray transmissivity Tp change according to the type of grid. Thus, a table in which a variety of subject information and virtual grid features are associated with each other is stored in the storage section 39, with respect to the subject information. The subject information may include information relating to a position of a subject on a radiographic image, a composition distribution of the subject, the size and thickness of the subject, in addition to the type of the subject.

The feature acquisition imaging condition includes at least one of an imaging distance (SID) in imaging, the amount of imaging rays, a tube voltage, materials of a target of a radiation source and a filter, the type of a radiation detector to be used in imaging, and the like. Here, when capturing the subject image Ik, the type of the grid to be used is generally determined according to the imaging condition, and the scattered ray transmissivity Ts and the primary ray transmissivity Tp change according to the type of the grid. Thus, a table in which various feature acquisition imaging conditions and virtual grid features are associated with each other is stored in the storage section 39, with respect to the feature acquisition imaging condition. As long as the feature acquisition imaging condition includes parameters necessary for acquisition of the virtual grid features, the feature acquisition imaging condition may be the same as an imaging condition used for determination of a thickness distribution (a thickness distribution determination imaging condition) or a scattered ray information acquisition imaging condition used for acquisition of scattered ray information, or may be different therefrom.

The feature acquisition section 34 acquires the virtual grid features based on at least one of the grid information, the subject information, and the feature acquisition imaging condition, input from the input section 41, with reference to the table stored in the storage section 39. The feature acquisition section 34 may directly receive inputs of the grid information, the subject information, and the feature acquisition imaging conditions through an input section 41, but a list of a variety of grid information, a variety of subject information, and various feature acquisition imaging conditions may be displayed on the display section 42, and at least one selection of grid information, subject information, and a feature acquisition imaging condition from the list may be received to perform input of the grid information, the subject information, and the feature acquisition imaging condition.

Further, in the second embodiment, the scattered ray removal process is performed by frequency-resolution of the subject image Ik as described later. In the second embodiment, the feature of a virtual grid is acquired with respect to each of plural frequency bands of the subject image Ik acquired by the frequency resolution. Thus, the virtual grid features in the table are associated with each of the plural frequency bands.

Further, a table in which all of the grid information, the subject information and the feature acquisition imaging conditions are associated with the virtual grid features may be stored in the storage section 39, and the virtual grid features may be acquired based on all of the grid information, the subject information, and the feature acquisition imaging conditions. In this case, the table is formed as an at least four-dimensional table in which the variety of grid information, the variety of subject information, the various feature acquisition imaging conditions, and the virtual grid features are associated with each other.

An exposure magnifying factor which is a proportional increase in the amount of emitted rays that increases as a grid is used, a contrast improvement coefficient which is the ratio of contrast when the grid is used to contrast when the grid is not used, and a selectivity which is the ratio of a primary ray transmissivity to a scattered ray transmissivity are feature values indicating features of the grid. The scattered ray transmissivity Ts and the primary ray transmissivity Tp may be calculated from these feature values. Thus, as at least one designation of the exposure magnifying factor, the contrast improvement coefficient, and the selectivity is received in the feature acquisition section 34, the virtual grid features, that is, the scattered ray transmissivity Ts and the primary ray transmissivity Tp may be calculated and acquired.

Further, in the second embodiment, the image processing device 30 performs the scattered ray removal process based on scattered ray information in addition to the virtual grid features. Thus, the scattered ray information acquisition section 35 further acquires scattered ray information as the scattered ray information. In the second embodiment, for example, if the subject K is a chest portion, the scattered ray information shows a scattered ray content distribution in a subject image Ik, in which there is a large amount of scattered rays in a central portion of the subject image Ik where a mediastinal space is present and there is a small amount of scattered rays in a peripheral portion where a lung field is present.

The scattered ray information acquisition section 35 analyzes a subject image Ik acquired by imaging to obtain scattered ray information, that is, a scattered ray content distribution.

The scattered ray information acquisition section 35 calculates a primary ray component Ip(x, y) and a scattered ray component Is(x, y) in each position according to Expression (1) from a thickness distribution Tk(x, y) of a subject K and an imaging condition in radiography of a subject image Ik, similar to the first embodiment, and calculates a scattered ray content distribution S(x, y) according to Expression (4) from the calculated primary ray component Ip(x, y) and scattered ray component Is(x, y). The scattered ray content distribution S(x, y) has values of 0 to 1. In the second embodiment, Expression (3) may be used instead of Expression (1). That is, as shown in Expression (3), since the scattered ray estimation function includes the primary ray estimation function for estimating the pixel value Ip(x', y') of the primary ray component in each position in the non-shielded image area RA based on the index attenuation rule and setting the pixel value Ip(x', y') of the primary ray component in each position in the shielded image area RB to zero, it is possible to reflect the condition indicating that scattered rays from the shielded subject portion KB are not present in the scattered ray estimation function.

$$S(x,y)=Is(x,y)/(Is(x,y)+Ip(x,y)) \quad (4)$$

In the second embodiment, in Expression (2), an incident amount Io(x, y) of radioactive rays with respect to a surface of a subject is cancelled out by division when S(x, y) is calculated irrespective of the value defined for Io(x, y). Thus, for example, Io(x, y) may have an arbitrary value, for example, 1.

The removal processing section 36 performs a scattered ray removal process by reducing a frequency component in a frequency band which can be considered as scattered rays in a subject image Ik based on virtual grid features and scattered ray information. Thus, the removal processing section 36 frequency-resolves the subject image Ik to obtain a frequency component for each of plural frequency bands, performs a process of reducing a gain of at least one frequency component, and synthesizes the processed frequency component and other frequency components to obtain a subject image Ik which is subjected to the scattered ray removal process. As a frequency-resolution method, a method for performing multiple resolution conversion with respect to a subject image Ik may be used. Further, a known arbitrary method such as wavelet transform or Fourier transform may be used.

The removal processing section 36 calculates a conversion coefficient R(x, y) for converting a frequency component from the scattered ray transmissivity Ts and the primary ray transmissivity Tp which are the virtual grid features, and from the scattered ray content distribution S(x, y) using the following Expression (5). Since the scattered ray transmissivity Ts represents a transmission rate of a scattered ray component assuming that the entire scattered ray component is 1, a first ratio indicating reduction of the scattered ray component is represented as 1−Ts. Similarly, since the primary ray transmissivity Tp represents a transmission rate of a primary ray component assuming that the entire primary ray component is 1, a second ratio indicating reduction of the primary ray component is represented as 1−Tp. The second ratio is set to be equal to or smaller than the first ratio, and the proportion of the first ratio and the second ratio is appropriately set to achieve a desired scattered ray suppression result.

$$R(x,y)=S(x,y)\times Ts+(1-S(x,y))\times Tp \qquad (5)$$

Since the scattered ray transmissivity Ts and the primary ray transmissivity Tp, and the scattered ray content distribution S(x, y) have values of 0 to 1, the conversion coefficient R(x, y) also becomes a value of 0 to 1. The removal processing section 36 calculates the conversion coefficient R(x, y) for each of the plural frequency bands.

In the following description, a pixel value of a subject image Ik is represented as Ik(x, y), a frequency component image acquired by frequency resolution is represented as Ik(x, y, r), a frequency synthesis is represented as Ik(x, y)=ΣrIk(x, y, r), a conversion coefficient for each frequency band is represented as R(x, y, r), and a scattered ray transmissivity and a primary ray transmissivity for each frequency band are represented as Ts(r) and Tp(r). Here, r represents a layer of a frequency band. As r becomes larger, the frequency is low. Accordingly, Ik(x, y, r) represents a frequency component image in a certain frequency band. The scattered ray content distribution S(x, y) may employ a value calculated with respect to a subject image Ik, and may be acquired with respect to each of the frequency bands, similar to the scattered ray transmissivity Ts and the primary ray transmissivity Tp.

In the second embodiment, the conversion coefficient R(x, y, r) is calculated for each frequency component, the frequency component image Ik(x, y, r) is multiplied by the conversion coefficient R(x, y, r) of a corresponding frequency band to convert a pixel value of the frequency component image Ik(x, y, r), and the frequency component images Ik(x, y, r) multiplied by the conversion coefficients R(x, y, r) (that is, Ik(x, y, r)×R(x, y, r)) are frequency-synthesized to obtain a processed subject image Ik'(x, y). Accordingly, the process performed in the removal processing section 36 is expressed by the following Expression (6). Since the conversion coefficient R(x, y, r) has a value of 0 to 1, as the frequency component Ik(x, y, r) is multiplied by the conversion coefficient R(x, y, r) of the corresponding frequency band, a pixel value at the pixel position (x, y) of the frequency component, that is, a gain is reduced.

$$Ik'(x, y) = \sum r\{Ik(x, y, r) \times R(x, y, r)\} \qquad (6)$$
$$= \sum r\{Ik(x, y, r) \times (S(x, y) \times Ts(r) + (1 - S(x, y)) \times Tp(r))\}$$

Here, in the second embodiment, it is assumed that a subject image Ik is frequency-resolved into six frequency bands and the scattered ray transmissivity Ts and the primary ray transmissivity Tp are acquired with respect to six frequency bands. In this case, the scattered ray transmissivity Ts and the primary ray transmissivity Tp become values as shown in the following Expression (7). In Expression (7), a value of a lower frequency band is written as it goes to the right side.

$$Ts=\{0.7,0.7,0.7,0.7,0.3,0.2\}$$
$$Tp=\{0.7,0.7,0.7,0.7,0.7,0.7\} \qquad (7)$$

As shown in Expression (7), the scattered ray transmissivity Ts and the primary ray transmissivity Tp have the same values at high frequency bands (r=1 to 4), but the scattered ray transmissivity Ts becomes a lower value at low frequency bands (r=5 to 6). This is because a grid has a high removal rate but has a removal efficiency with respect to primary rays with little dependency on frequency in a low frequency band where a frequency component of scattered rays is dominant.

For example, in the case of a subject image of a chest portion obtained through radiography, in a mediastinal portion and a peripheral portion of a lung field where the content of scattered rays is high, a value of the conversion coefficient calculated based on Expressions (5) and (7) becomes smaller, and a pixel value is greatly reduced. Accordingly, in a processed scattered ray suppressed image Ik' acquired by performing the process shown in Expression (6) using the calculated conversion coefficient, the scattered ray component is removed according to the type of a grid to be used.

The removal processing section 36 may remove scattered rays of a subject image Ik as follows. First, when the frequency synthesis is represented as Ik(x, y)=ΣrIk(x, y, r) as described above, the removal processing section 36 resolves the frequency component image Ik(x, y, r) into a scattered ray component Is(x, y, r) (a pixel value corresponding to the scattered ray component) and a primary ray component Ip(x, y, r) (a pixel value corresponding to the primary ray component) using the scattered ray content distribution S(x, y) according to the following Expression (8).

$$Is(x,y,r)=S(x,y)\times Ik(x,y,r)$$
$$Ip(x,y,r)=(1-S(x,y))\times Ik(x,y,r) \qquad (8)$$

Further, the removal processing section 36 respectively applies a scattered ray transmissivity Ts(r) and a primary ray transmissivity Tp(r) which are virtual grid features to the scattered ray component Is(x, y, r) and the primary ray component Ip(x, y, r) for image conversion, and calculates a converted scattered ray component Is'(x, y, r) and a converted primary ray component Ip'(x, y, r) by Expression (9).

$$Is''(x,y,r)=Is(x,y,r) \times Ts(r)=S(x,y) \times Ik(x,y,r) \times Ts(r)$$

$$Ip'(x,y,r)=Ip(x,y,r) \times Tp(r)=(1-S(x,y)) \times Ik(x,y,r) \times Tp(r) \qquad (9)$$

Further, Is'(x, y, r) and Ip'(x, y, r) are frequency-synthesized according to the following Expression (10) to calculate a scattered ray suppressed image Ik(x, y)' through the scattered ray suppression process.

$$Ik'(x, y) = \sum r\{Is'(x, y, r) + Ip'(x, y, r)\} \qquad (10)$$
$$= \sum r\{S(x, y) \times Ik(x, y, r) \times Ts(r) + (1 - S(x, y)) \times Ik(x, y, r) \times Tp(r)\}$$
$$= \sum r\{Ik(x, y, r) \times (S(x, y) \times Ts(r) + (1 - S(x, y)) \times Tp(r))\}$$

Next, a process performed in the second embodiment will be described. FIG. 6 is a flowchart illustrating a process performed in the second embodiment. If a subject image Ik acquired in the imaging device 10 is input to the image processing device 30, the image acquisition section 31 acquires the subject image Ik (step ST21). Then, the area information acquisition section 32 acquires area information corresponding to the subject image Ik (step ST22). Subsequently, the scattered ray suppression section 33 receives at least one input from the input section 41 among grid information, subject information, and an imaging condition by the feature acquisition section 34, and to acquire virtual grid features, that is, a scattered ray transmissivity Ts and a primary ray transmissivity Tp (ST23).

Further, the scattered ray information acquisition section 35 estimates a scattered ray component and a primary ray component in each position based on the imaging condition, the area information, and the conditional Expressions (1) and (2), and acquires scattered ray component information, that is, a scattered ray content distribution S(x, y) based on the estimated scattered ray component and primary ray component (ST24). On the other hand, the removal processing section 36 frequency-resolves the subject image Ik. The processes of step S23, step S24, and step S25 may be performed in an arbitrary order, or may be performed in parallel.

Further, the removal processing section 36 calculates a conversion coefficient R(x, y, r) for each frequency band using Expression (5) (ST25), and converts the frequency component image Ik(x, y, r) using the conversion coefficient R(x, y, r) to suppress the scattered ray component (ST26). Further, the removal processing section 36 frequency-synthesizes the converted frequency component image Ik'(x, y, r) to generate a scattered ray suppressed image Ik' (step ST27). Then, the removal processing section 36 stores the scattered ray suppressed image Ik' in the storage section 39, and then terminates the process. Thereafter, the image processing device 30 performs predetermined image processing such as noise removal, grayscale processing and frequency processing on the scattered ray suppressed image as necessary to obtain a processed image, and stores the processed image in the storage section 39. Further, when a display request is received from a user, the image processing device 30 displays the processed image in the display section 42.

According to the second embodiment, since the scattered ray suppression section 33 separates a pixel value in each position in the non-shielded image area RA into a scattered ray component and a primary ray component, reduces, in each position in the non-shielded image area RA, a scattered ray component corresponding to a first ratio from the scattered ray component at the position, and reduces a primary ray component corresponding to a second ratio which is equal to or smaller than the first ratio from the primary ray component at the position as necessary, to thereby suppress the scattered ray component in each position in the non-shielded image area RA, it is possible to reduce erroneous estimation of the scattered ray component in each position in the subject image, and to appropriately suppress the scattered ray component from the subject image by adjusting the ratio of the scattered ray component and the primary ray component in each position to be a desired ratio.

The scattered ray suppression section 33 according to the second embodiment acquires virtual grid features which are features of a grid to be used for removal of scattered rays when a subject image Ik is captured, acquires scattered ray component information, and performs a scattered ray removal process of the subject image Ik based on the virtual grid features and the scattered ray component information. Thus, with respect to a subject image captured without using a grid, it is possible to provide the same scattered ray removal effect as in a case where imaging is actually performed using the grid. Further, it is possible to make the image quality of the subject image Ik close to the image quality of a subject image acquired by performing imaging using various types of scattered ray removal grids.

Further, when a convergence type grid is used, there is a concern that density unevenness may occur in the subject image Ik due to oblique incidence of radioactive rays. However, in the second embodiment, by performing a process of removing scattered rays with respect to a subject image captured without using a grid, it is possible to prevent the occurrence of density unevenness due to oblique incidence of radioactive rays, and thus, it is possible to acquire a scattered ray suppressed image Ik' with higher quality.

Further, various modifications performed in a range without departing from the spirit of the invention with respect to the system configurations, the hardware configurations, the processing flows, the module configurations, the user interfaces, the specific processing contents, and the like in the above-described embodiments are also included in the technical scope of the invention. For example, a part or the entirety of the components of the image analysis device may be configured by a single workstation, or may be configured by one or more workstations, a server, and a storage device which are connected to each other through a network. Further, in order to acquire a thickness distribution, an arbitrary method may be employed. For example, a thickness distribution acquisition method disclosed in Japanese Patent Application No. 2013-229941, Japanese Patent Application No. 2013-229942, or the like may be employed.

Further, in the above-described embodiments, the scattered ray removal process is performed using a radiographic image acquired in the imaging device 10 that captures a radiographic image of a subject using the detector 14, but as disclosed in JP1996-266529A (JP-H8-266529A), JP1997-24039A (JP-H9-24039A), or the like, even in a case where radiographic image information of a subject is cumulatively recorded on a storage fluorescent sheet which is a radiation detector and a radiographic image acquired from the storage fluorescent sheet by photoelectric reading is used, the invention may be applied.

What is claimed is:

1. A radiographic image processing device comprising:
an image acquisition section that acquires a subject image which is a radiographic image captured by an imaging system that includes a radiation source that irradiates a subject with radioactive rays, a shield that partially shields the radioactive rays emitted to the subject, and a radiation detector that detects the radioactive rays passed through the subject, the subject image being detected under a predetermined imaging condition by a shielded detection portion which is a portion of the radiation detector where the radioactive rays are shielded by the shield in an irradiation direction of the radioactive rays from the radiation source and a non-shielded detection portion which is a portion of the radiation detector excluding the shielded detection portion;
an area information acquisition section that acquires area information which is information for specifying a non-shielded image area indicating a pixel value corresponding to each position in the non-shielded detection portion in the subject image and a shielded image area indicating a pixel value corresponding to each position in the shielded detection portion in the subject image; and
a scattered ray suppression section that estimates, based on the imaging condition and the area information, spreading of scattered rays generated in a non-shielded subject portion which is a portion of the subject that transmits the radioactive rays in the irradiation direction of the radioactive rays from the radiation source in the subject image, estimates that scattered rays that spread to the non-shielded image area from a shielded subject portion which is a portion of the subject where the radioactive rays are shielded by the shield in the irradiation direction of the radioactive rays from the radiation source are not present, calculates a scattered ray component in each position in the non-shielded image area as the estimated scattered rays reach each position in the non-shielded image area, and suppresses the scattered ray component in each position in the non-shielded image area according to the calculated scattered ray component.

2. The radiographic image processing device according to claim 1,
wherein the scattered ray suppression section estimates a spread distribution indicating spreading of scattered rays according to a primary ray component in each position in the subject image, and calculates the scattered ray component in each position in the non-shielded image area using a scattered ray estimation function for estimating a sum of scattered rays that reach each position in the non-shielded image area as a scattered ray component at the position, based on the estimated spread distribution of the scattered rays, with respect to each position in the non-shielded image area.

3. The radiographic image processing device according to claim 2,
wherein the scattered ray suppression section sets a first condition for negating the arrival of the scattered rays from the shielded subject portion in the scattered ray estimation function to estimate that the scattered rays that spread to the non-shielded image area from the shielded subject portion are not present.

4. The radiographic image processing device according to claim 2,
wherein the scattered ray suppression section sets a second condition for setting the primary ray component in each position in the shielded image area to zero in the scattered ray estimation function to estimate that the scattered rays that spread to the non-shielded image area from the shielded subject portion are not present.

5. The radiographic image processing device according to claim 1,
wherein the scattered ray suppression section subtracts the scattered ray component in each position in the non-shielded image area from a pixel value in each corresponding position in the non-shielded image area to suppress the scattered ray component in each position in the non-shielded image area.

6. The radiographic image processing device according to claim 2,
wherein the scattered ray suppression section subtracts the scattered ray component in each position in the non-shielded image area from a pixel value in each corresponding position in the non-shielded image area to suppress the scattered ray component in each position in the non-shielded image area.

7. The radiographic image processing device according to claim 3,
wherein the scattered ray suppression section subtracts the scattered ray component in each position in the non-shielded image area from a pixel value in each corresponding position in the non-shielded image area to suppress the scattered ray component in each position in the non-shielded image area.

8. The radiographic image processing device according to claim 4,
wherein the scattered ray suppression section subtracts the scattered ray component in each position in the non-shielded image area from a pixel value in each corresponding position in the non-shielded image area to suppress the scattered ray component in each position in the non-shielded image area.

9. The radiographic image processing device according to claim 1,
wherein the scattered ray suppression section separates a pixel value in each position in the non-shielded image area into a scattered ray component and a primary ray component, reduces, in each position in the non-shielded image area, a scattered ray component corresponding to a first ratio from the scattered ray component at the position, and reduces a primary ray component corresponding to a second ratio which is equal to or smaller than the first ratio from the primary ray component at the position, to suppress the scattered ray component in each position in the non-shielded image area.

10. The radiographic image processing device according to claim 2,
wherein the scattered ray suppression section separates a pixel value in each position in the non-shielded image area into a scattered ray component and a primary ray component, reduces, in each position in the non-shielded image area, a scattered ray component corresponding to a first ratio from the scattered ray component at the position, and reduces a primary ray component corresponding to a second ratio which is equal to or smaller than the first ratio from the primary ray component at the position, to suppress the scattered ray component in each position in the non-shielded image area.

11. The radiographic image processing device according to claim 3,
wherein the scattered ray suppression section separates a pixel value in each position in the non-shielded image area into a scattered ray component and a primary ray component, reduces, in each position in the non-shielded image area, a scattered ray component corresponding to a first ratio from the scattered ray component at the position, and reduces a primary ray component corresponding to a second ratio which is equal to or smaller than the first ratio from the primary ray component at the position, to suppress the scattered ray component in each position in the non-shielded image area.

12. The radiographic image processing device according to claim 4,
wherein the scattered ray suppression section separates a pixel value in each position in the non-shielded image area into a scattered ray component and a primary ray component, reduces, in each position in the non-shielded image area, a scattered ray component corresponding to a first ratio from the scattered ray component at the position, and reduces a primary ray component corresponding to a second ratio which is equal to or smaller than the first ratio from the primary ray component at the position, to suppress the scattered ray component in each position in the non-shielded image area.

13. A radiographic image processing method executed in a radiographic image processing device, comprising:
acquiring a subject image which is a radiographic image captured by an imaging system that includes a radiation source that irradiates a subject with radioactive rays, a shield that partially shields the radioactive rays emitted to the subject, and a radiation detector that detects the radioactive rays passed through the subject, the subject image being detected under a predetermined imaging condition by a shielded detection portion which is a portion of the radiation detector where the radioactive rays are shielded by the shield in an irradiation direction of the radioactive rays from the radiation source and a non-shielded detection portion which is a portion of the radiation detector excluding the shielded detection portion;
acquiring area information which is information for specifying a non-shielded image area indicating a pixel value corresponding to each position in the non-shielded detection portion in the subject image and a shielded image area indicating a pixel value corresponding to each position in the shielded detection portion in the subject image; and
estimating, based on the imaging condition and the area information, spreading of scattered rays generated in a non-shielded subject portion which is a portion of the subject that transmits the radioactive rays in the irradiation direction of the radioactive rays from the radiation source in the subject image, estimating that scattered rays that spread to the non-shielded image area from a shielded subject portion which is a portion of the subject where the radioactive rays are shielded by the shield in the irradiation direction of the radioactive rays from the radiation source are not present, calculating a scattered ray component in each position in the non-shielded image area as the estimated scattered rays reach each position in the non-shielded image area, and suppressing the scattered ray component in each position in the non-shielded image area according to the calculated scattered ray component.

14. A non-transitory computer-readable recording medium that stores a radiographic image processing program that causes a computer to function as:
an image acquisition section that acquires a subject image which is a radiographic image captured by an imaging system that includes a radiation source that irradiates a subject with radioactive rays, a shield that partially shields the radioactive rays emitted to the subject, and a radiation detector that detects the radioactive rays passed through the subject, the subject image being detected under a predetermined imaging condition by a shielded detection portion which is a portion of the radiation detector where the radioactive rays are shielded by the shield in an irradiation direction of the radioactive rays from the radiation source and a non-shielded detection portion which is a portion of the radiation detector excluding the shielded detection portion;
an area information acquisition section that acquires area information which is information for specifying a non-shielded image area indicating a pixel value corresponding to each position in the non-shielded detection portion in the subject image and a shielded image area indicating a pixel value corresponding to each position in the shielded detection portion in the subject image; and
a scattered ray suppression section that estimates, based on the imaging condition and the area information, spreading of scattered rays generated in a non-shielded subject portion which is a portion of the subject that transmits the radioactive rays in the irradiation direction of the radioactive rays from the radiation source in the subject image, estimates that scattered rays that spread to the non-shielded image area from a shielded subject portion which is a portion of the subject where the radioactive rays are shielded by the shield in the irradiation direction of the radioactive rays from the radiation source are not present, calculates a scattered ray component in each position in the non-shielded image area as the estimated scattered rays reach each position in the non-shielded image area, and suppresses the scattered ray component in each position in the non-shielded image area according to the calculated scattered ray component.

* * * * *